US005676684A

United States Patent [19]

Choi

[11] Patent Number: 5,676,684

[45] Date of Patent: Oct. 14, 1997

[54] METHOD AND APPARATUS FOR ACUPUNCTURE-TAPPING PORTION OF HUMAN

[76] Inventor: Jang Youn Choi, Haebaraki Villa 4-102, 632-2, Deungchon-dong, Kangsu-gu, Seoul 157-030, Rep. of Korea

[21] Appl. No.: 728,737

[22] Filed: Oct. 11, 1996

Related U.S. Application Data

[63] Continuation of Ser. No. 284,625, filed as PCT/KR93/00011, Feb. 11, 1993, abandoned.

[30] Foreign Application Priority Data

Feb. 20, 1992 [KR] Rep. of Korea ........................ 92-2518

[51] Int. Cl.$^{6}$ .................................................... A61B 17/34

[52] U.S. Cl. ............................................ 606/189; 128/907

[58] Field of Search .................................... 606/169, 189, 606/185, 186, 204; 128/735, 907; 81/9.22

[56] References Cited

U.S. PATENT DOCUMENTS

| | | | |
|---|---|---|---|
| 55,775 | 6/1866 | Klee | 606/186 |
| 4,112,923 | 9/1978 | Tomecek | 600/11 |
| 4,204,438 | 5/1980 | Binaris et al. | 81/9.22 |
| 4,286,599 | 9/1981 | Hahn et al. | |
| 4,549,535 | 10/1985 | Wing | 601/108 |
| 4,914,988 | 4/1990 | Chang | 81/9.22 |
| 4,961,421 | 10/1990 | Muller | 606/180 |
| 5,140,979 | 8/1992 | Nakagawa | 601/108 |
| 5,250,067 | 10/1993 | Gelfer et al. | 606/189 |

FOREIGN PATENT DOCUMENTS

| | | |
|---|---|---|
| 0584297 | 2/1925 | France . |
| 0846767 | 7/1949 | Germany . |
| 2234420 | 2/1991 | United Kingdom . |

*Primary Examiner*—Michael Buiz
*Assistant Examiner*—Patrick W. Rasche
*Attorney, Agent, or Firm*—Michael N. Meller

[57] ABSTRACT

A method and apparatus for acupuncture-tapping procedures on a human body. The apparatus includes an acupuncture-tapping plate which has attached needles. A buffer connector is attached to the acupuncture-tapping plate solely by resilient member. A driving member is attached to the buffer connector by resilient member so that the buffer connector is operated to drive the acupuncture-tapping plate by utilizing the buffer connector. In this way, an acupuncture-tapping technique is provided which has beneficial effects on the damaged skin of the human body.

4 Claims, 2 Drawing Sheets

METHOD AND APPARATUS FOR ACUPUNCTURE-TAPPING PORTION OF HUMAN

This application is a continuation of application Ser. No. 08/284,625, filed as PCT/KR93/00011 Feb. 11, 1993 now abandoned.

FIELD OF THE INVENTION

The present invention relates to an acupuncture-tapping apparatus. In particular, it concerns an acupuncture-tapping apparatus comprising an acupuncture-tapping part including an acupuncture-tapping plate having various needles attached, a buffer connector, a driving part, a handle and if necessary, an additional support part, which improves one's physical condition and prevents the diseases.

BACKGROUND OF THE INVENTION

There has been no special tapping theory existing before the present inventor established such theory. The old instruments for tapping have been those poorly made from a bamboo or plastic, which is too simple to compete with the acupuncture-tapping apparatus of the present invention. Also, the old tapping instruments are quite different from the acupuncture-tapping apparatus of the present invention with respect to function and structure.

The present invention is based on the theories of physiotherapy which have maintained human health such as acupuncture & moxibustion, Buhang(suction therapy after acupuncturing for suction of virulent blood and abnormal force-energy into a jar), finger-pressure(manual) therapy, X-ray or light projecting therapy, electromagnetic therapy.

Although "the tapping method" and the acupuncture-tapping method asserted by the present inventor may be recognized to be entirely unfamiliar since it has never been theorized yet, a tapping method is well known. Massage is a kind of tapping method. Generally, people tap or massage a pain region in order to remove pain. The very action is a kind of tapping method.

However, it is natural that when one person beats another on the whole body including his head for the purpose of medical treatment, he may feel fear, discomfort, rejection symptom and the like. However, the present inventor found that the acupuncture-tapping therapy changes the abnormal state of a human body into normal one and moreover has an outstanding effect on improving human habitude-physical constitution through the clinical study to which he, his family and relatives have been subjected.

SUMMARY OF THE INVENTION

The present invention comprises applying repeatedly the needles of the acupuncture-tapping apparatus while controlling the rate at which the needles are applied to the skin. At the same time the heat, light and electromagnetism applied to the skin, peripheral nerve system and blood vessel is controlled to exchange, metastasis and reaction between a macro and a micro force-energy to normalize the abnormal force-energy, the passage of the fluid materials under the skin and the exchange, metastasis and reaction of materials and force-energy, resulting in the human body recovering to a normal condition.

It is an object of the present invention to provide an acupuncture tapping apparatus which improves the functions of each system, organ and tissue of patients into an optimum state, breaking out the traditional methods for directly treating abnormal symptoms, pain and the like in order to return the state of patients to normal.

It is another object of the present invention to provide an outstanding effect of acupuncture-tapping therapy.

DETAILED DESCRIPTION OF THE INVENTION

Figure 1:
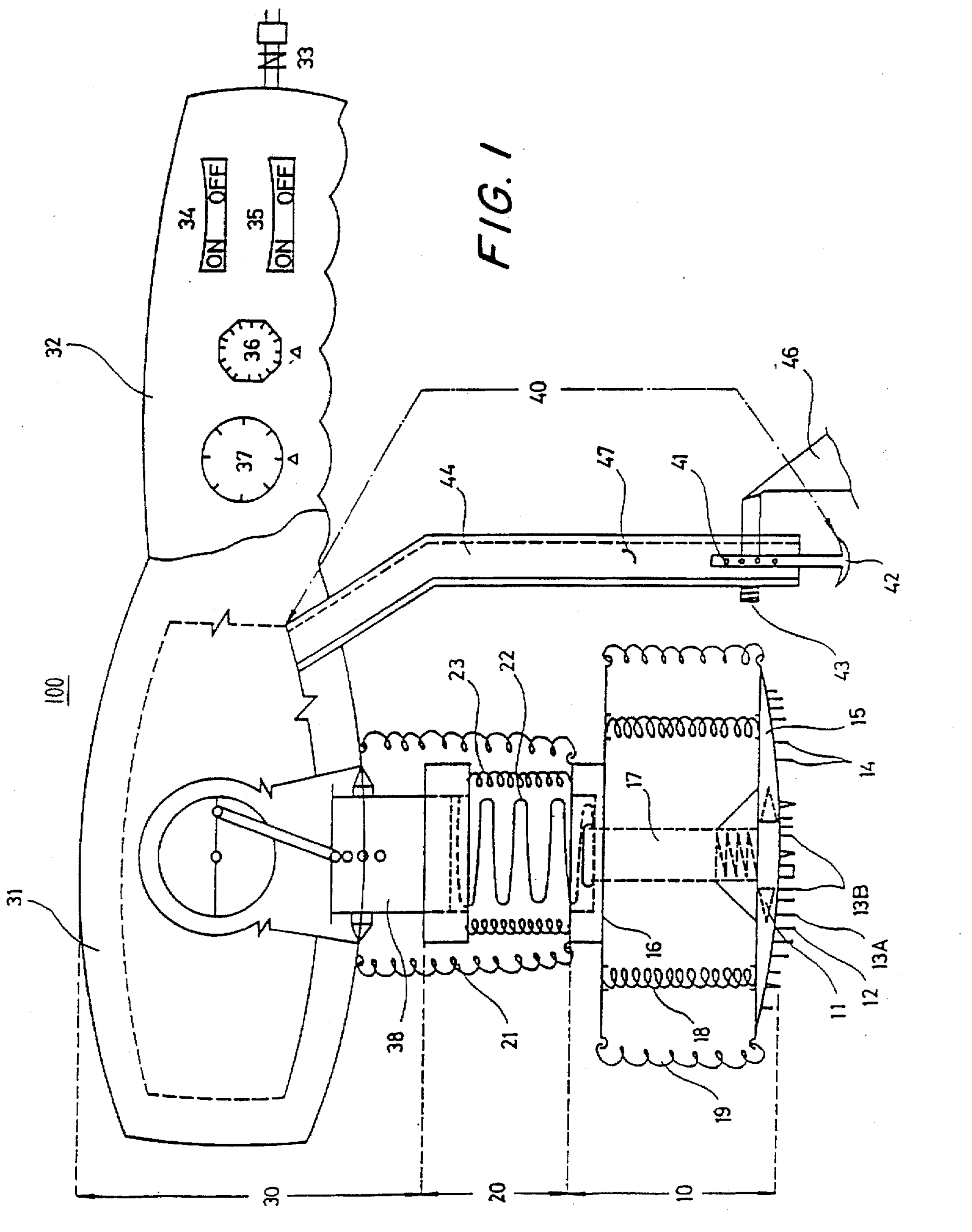
FIG. 1 is a side view of a preferred embodiment of the electromotive acupuncture-tapping apparatus of the present invention shown partially broken away.
Figure 2A:
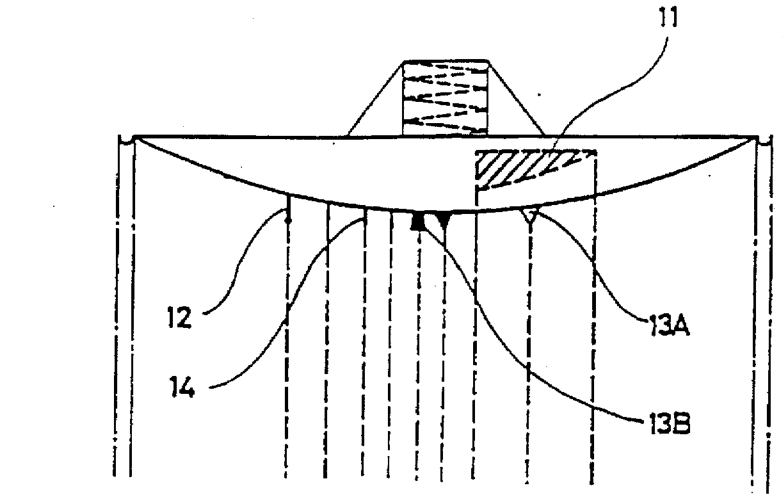
FIG. 2 contains FIG. 2(A) which is a side elevational view and FIG. 2(B) which is a plan view of the acupuncture-tapping plate shown in FIG. 1.
Figure 2B:
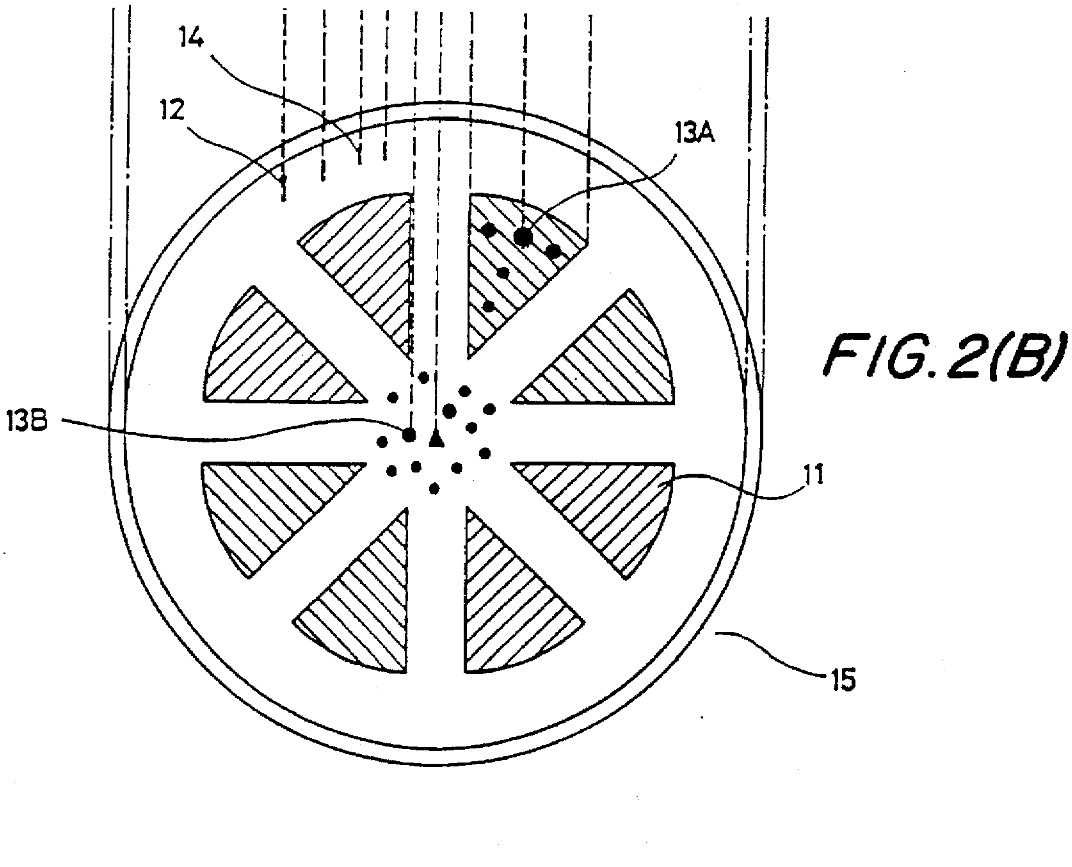

Assume that a human body is composed of systems, organs and tissues; materials organizing each tissue circulate through various paths of areas such as the area which synthesizes and decomposes molecules, the area where atomic physico-chemical reaction, exchange and metastasis occur, the area where the strong interaction, weak interaction, universal gravitation and electromagnetic force exchange with one another, the area where the integrating force is effective, the area of a limited dimensional system where the force-energy of each existence is effective and the area of the system of an unlimited dimension of spirit and mind. In addition, assume the human body includes the surpassed area(or One Wholeness) without time halt, existence and power, which surpasses cognition and imagination. In this way we can recognize there is always an exchange of force-energy between the system of spirit or mind and the system of materials themselves. Therefore, the definition of diseases in the present invention is the unbalance of the materials of the macro-system(One Wholeness) such as human intestines, muscle, skin, joints, nerves, cells and reacting materials in the human body and the unbalance of energy accompanied pain(ache), a chill, fever, dizziness, lethargy, anxiety, discomfort, insomnia, sleep-walking, illusion, hysteria and the like thereby in the micro-system (One Wholeness). That is the unbalance of the materials of the macro-system and unbalance of the energy of the micro system. The words such as interruption, superabundance, lack, rupture, interception, connection caused by exchange, reaction and metastasis between materials and the force-energy in the human body are consonant with the name of diseases. Therefore, it is natural that those diseases having such symptoms should be cured in the manner of tracking a path of each unit disease in reverse or regular order.

However, paths of any unit disease from its origin are very complicated and the factors of the micro-system acting on the paths are too many to count, so that the methods selected for prevention and remedy of the unit disease in the human body according to the concept of time are countless even among the areas such as medicinal therapy, operational therapy or physical therapy. The reason is that while paths of a unit disease are known in the human body, the paths may be known only as a virtual image outside the human body and the structure and capacity of each system, organ, tissue of the human body are different for different individuals. The reason that the paths are recognized as a virtual image is that all the factors of the disease in the human body are delivered to the outside of the human body and they are recognized by the paths through which they are delivered. Therefore, any remedy which considers the size, quality, quantity, speed and the like of the energy of the micro-system is not proper and should be naturally improved.

Just as we say that petroleum is energy, it is natural that we say that a human body is a force, i.e., energy. This expression may be strange enough but it implies the same meaning. Also, it is interesting to assume that there are exchange, reaction and metastasis of the microscopic force-energy which man can not see, hear and feel, and moreover such exchange, reaction and metastasis can also happen in the limited microscopic force-energy (One Wholeness) that transcends the force-energy mentioned above. There may be an interesting inference when applying those macroscopic materials and microscopic force-energy to individuals.

It is understandable that the total amount of materials and force-energy consumed keeping a human body force from diseases other than those materials and force-energy consumed only for survival, taste, stamina, promoting health from birth to death will reach into astronomical figures. Instead, if diseases are decreased by the effort, be free of them, it will be a decisive factor that will lengthen the time to consume the limited, usable resources being maintained by mankind.

The history flows toward new and more profitable future and knowledge on the basis of numerous beneficial knowledge accumulated in the past and the present. The more people there are who are not healthy and spend a lifetime without emission and absorption of mental energy in a nation, the weaker the power accumulated in the nation becomes and the greater the consumption of usable resources.

The basic theory of the present invention comprises the exchange, reaction and metastasis of the macroscopic force-energy in accordance with tapping acupunctures, and the exchange of the microscopic force energy of heat, light and electromagnetism.

It assumes that men living on one point of the earth receive almost constant electro-magnetic force throughout their lifetime. For example, it is understandable that since the Korean Peninsula is located between 32° and 43° N. latitude, macrospically it belongs to the scope of the force-energy which is inclined to the direction of the N.pole.

Also, according to one of the ancient theories, the theory of geomancy which is closely related to gravitation and electromagnetic force, unfortune by water(an oriental theory) can be avoided by selecting Yin(negative) or Yang (positive) and the point on the earth where the quality of earth is optimum and topography is in the optimum balance of life will be found by the same. From such a theory, we know how gravitation and electromagnetic force have been considered and closely applied in real life since olden times and therefore, it gives us even nowadays very precious experience and teaching. However, most people nowadays live without the awareness of the fact that strong and weak interaction, gravitation, and electromagnetic force are related to and have influence on them. The fact that in every moment the force-energy of the external microscopic system exchanges energy with the parts of the microscopic human body will give a very significant meaning not only to the scholars who research the force-energy of the microscopic system but also to all people. As a new theory on One Wholeness theory, that the present inventor believes that the integration of all kinds of concept and thing or force-energy can be derived from the theory of triple-origin circulation. That is, the theory of triple-origin circulation can be simply described in the following drawing;

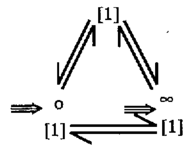

According to the theory, all the knowledge in natural science, human science, and sociology and even the information of civilization can be explained.

[1] The One Wholeness (= Han-Ool Nim = The creative and evolutionary Absolute)

⟹ o

[1] One Wholeness (It is closed to the mean of once of Wholeness. Infinitesimal-Microscopic System = Han-Ool)

⟹ ∞

[1] One Wholeness (It is closed to the mean of once of Wholeness. Universal System = Han-Ool)

When a part of human body is damaged by outer or inner power or a macroscopic disease occurs in a human body, one or more of the following may occur, changes of the pressure, concentration, distribution, moving speed, temperature and the like of fluid materials such as blood, mallow, hormone, water or aqueous solution comprising aqueous solution, suspension, emulsion or coagulation and the like of an organic or inorganic material in the damaged part, for example, in the intestinal area, skin and muscle area, joint area and brain area abnormally occur due to exchange, reaction and metastasis of force-energy. If this state does not recover immediately to a normal state and a long time passes in a state of lacking of its own capacity, the function of the tissues of the damaged part is macrospically decreased. Lastly, with the accelerating effect of inertia, the unbalance due to the unified system of both a macrosystem and a microsystem can be seen as the symptom of any disease. For instance, it is often seen that when someone's finger is carelessly injured by a hammer having a macroscopic strength, it has a bruise immediately. It is understandable that the damaged part of a human body which is given a considerable force in a moment maintains equilibrium by counteraction and many functions of the human body are self-mobilized to recover the original function. The functions of skin, hypodermic muscle and blood are mostly outstanding and a large amount of blood is mobilized at the same time. In this process, it is seen that the transferred blood is naturally overloaded, and that blood not recovered from the already mobilized makes the damaged part swell and causes pain with blood congested while time passes and then the coagulated blood becomes thrombotic and virulent. The recovery of the damaged part without external help takes a very long time. As the fluid materials, fibrous materials and solid materials in the damaged part become abnormal, it is natural that in order to recover rapidly the original state or function of the human body, the exchange, metastasis and reaction of force-energy and the fluidity, exchanges and metastasis of fluid materials should be made state normal state.

The present inventor is much experienced in acupuncture medical science and firmly believes that acupuncture therapy is never behind medicinal therapy and operational therapy in its effect. WHO(World Health Organization) admitted the 361 regions for acupuncture, 14 meridians about 1000 regions for acupuncture that have been newly established and thousands of movable regions.

However, the present inventor believes personally that all the parts of a human body can be a region for acupuncture and the force-energy can exchange, metastasis and react all over the body because the structure and capacity of each system, organ and tissue of individuals differ from each other.

Since the words used in an ancient Oriental medical science are considered to have validity in dealing with the force-energy of micro-system being exchanged in the human body, if the internal exchange, metastasis and reaction are equalized, the meaning of tapping acupuncture therapy will be extended and developed with the passage of time.

Referring to the drawing, the acupuncture-tapping apparatus(100) according to the present invention comprises an acupuncture-tapping part(10) including an acupuncture-tapping plate(15) having attached needles, a buffer connector(20), a driving part(30)for operating the buffer connector, a handle(32) including a power switch(34), a light switch(35) and current controllers(36,37) and if necessary, an additional support part(40).

The electromotive acupuncture-tapping apparatus(100) comprising an acupuncture-tapping part(10), a buffer connector(20), a driving part(30) and a support part(40) represents a the preferred embodiment of the present invention in FIG. 1.

The tapping part(10) of the apparatus of the present invention contains at least four needles per 1 $cm^2$ of a tapping plate(15) within an area of 200 $cm^2$ or less, the needles have a diameter of 0.5 to 5 mm and a length of 1 to 10 mm.

The needles of the present invention are selected from the group consisting of non-electromagnetic conductive needles (13A), electromagnetic semiconductive needles(13B), electrically conductive needles(14), magnetic conductive needles(12), magnetic needles and magnets(11 ).

The acupuncture-tapping part(10) of the apparatus(100) consists of an upper plate(16) centered about an adjustment screw(17) and a lower plate(15) as the acupuncture-tapping plate. The upper plate and the lower plate of the tapping part(10) are connected by buffer springs(18) with each other. The outside of the tapping part(10) is surrounded by sound- and shock-proof corrugated rubber(19).

The buffer connector(20) of the apparatus(100) according to the present invention consists of a main spring(22) for buffering the spring(22) connect top of the adjustment screw(17) with a piston(38) of the driving part(30). Minor springs (23) are provided between the piston(38) and the tapping part(10) and a sound- and shock-proof corrugated rubber(21) surrounds the outside of the buffer connector (20).

The driving part(30) of the apparatus(100) according to the present invention includes a motor(31) as a rotary motion member which is electrically operated to make the piston(38) linked with the buffer connector(20) go up and down. The mechanically operated piston(38) may also be a pneumatic air operated piston. The handle(32) of the apparatus(100) includes a power switch(34) for the motor (31), a switch(35) for a light, a current controller(36) for the electroconductive needles, a current controller(37) for the motor and a main power connecting cord(33).

According to the present invention, a support part(40) may be connected to the driving part(30). The support part(40) includes a height-controllable support(44) one end of which has a roller or sliding plate(42) attached by a control screw(41). The support(44) may have a bulb socket (43) for a light bulb, the screen(46) for covering a light and heat and a fixed hanger (47) for an ice bag.

The method of using the apparatus(100) of the present invention comprises arranging the apparatus(100), i.e., the tapping plate(15) having various needles attached, on to a damaged part or a skin requiring tapping adjusting the roller or sliding plate(42) of the support(44) depending on a desired region and turning on the switches(34, 35) for the current and light, resulting in a rotary motion of the driving part(30) to move the piston(38) of the driving part(30) upward and downward.

When the piston(38) moves up and down, the sound- and shock-proof corrugated rubber(21 ) of the buffer connector (20), the main spring and the minor springs(23) move simultaneously so that the motion is transferred to the tapping part(10) through the adjustment screw(17) linked with the buffer connector(20). Accordingly, it causes the tapping plate(15) of the tapping part(10) which is attached various needles to tap the skin.

The time using the acupuncture-tapping apparatus of the present invention may be adjusted depending on the state of the damaged part and the part required for tapping in human body.

Prior to tapping, an oil or vaseline may be applied to the skin.

The feature of the acupuncture-tapping apparatus according to the present invention is to improve the health of the skin and the constitution of the human body on the basis of the acupuncture-tapping therapy using properly the effect of the arrangement, size, number and flexibility of the needles, and the buffer effect, heat, light and electro-magnetic of the tapping plate(15).

When using the acupuncture-tapping apparatus, the tapping starts from hands or feet applying weakly on the part of severe pain until the body accepts the tapping moderately, then increasing intensity until the skin appears to be light pink. The time used in a day is not limited and acupuncture-tapping may apply on the whole body including the damaged part after several days or weeks from the day of the first application of acupuncture.

The tapping therapy of the present invention may use together with warm therapy and cold therapy. The acupuncture-tapping apparatus of the present invention represents stronger stimulation and more immediate effect than the traditional acupuncture apparatus. And for the extensive treatment of the human body, the acupuncture-tapping therapy has more outstanding merits than the existing physical therapy, i.e., acupuncture & moxibustion.

In addition, the acupuncture-tapping therapy according to the present invention excludes rejection symptoms due to the effect of the needle in the traditional acupuncture therapy and the bleeding in buhang therapy (extraction of virulent blood into a jar), the shamefulness in finger-pressure (manual) therapy and the side effects of X-ray and electricity-applying therapy.

The tapping therapy of the present invention is especially suited for those patients who have diseases of adult people, intractable diseases, diseases requiring a long period of recovery and diseases subject to possible sequelae. If even those who think they have no disease apply this tapping acupuncture continuously, it is possible they will regain the health of youth and live longer.

The acupuncture-tapping therapy according to the present invention may prevent or treat cancers and all the diseases in the systems of skin, respiration, digestion, blood circulation, nerves, muscle and endocrine glands. The acupuncture-tapping therapy has a superior effect in improving physical condition and preventing diseases, and the treatment effect is far better than other physical therapies.

The present inventor has clinically confirmed that the effect of the acupuncture-tapping therapy of the present invention is better than exercising taking tonics and medicines for promoting nutrition, in order to prevent diseases.

However, before proceeding with the acupuncture-tapping therapy of the present invention, those, who want to improve their physical condition and cure their diseases are required to acquire the basic knowledge of the human body and the theory of acupuncture, that is, the basic reasons or principles that the needle is put into the skin so that the painful part and the abnormal system and organ can be cured through the exchange, metastasis and reaction of force-energy.

As explained above, the acupuncture-tapping therapy is a new dimensional therapy which is grafted onto the acupuncture as one of Oriental medical sciences and the physical therapy as one of modern medical sciences.

According to the present invention, the abnormal condition of the human body can recover by the acupuncture-tapping therapy which helps the exchange of force-energy so as to efficiently utilize a proper quantity of food in the system, organ and tissue of the human body and normalize between materials and the system of materials, materials and the system of force-energy and force-energy and the system of force-energy, not by materials such as tonics, medicines for promoting nutrition. The further effect of the acupuncture-tapping therapy is to protect beneficial microorganisms in the body and change the unidentified microorganisms to have the high adaptability to the body, with results that weakens and kills harmful microorganisms, enhances immunity against diseases and prevents or delays aging.

What is claimed is:

1. An acupuncture-tapping apparatus comprising an acupuncture-tapping member including an upper plate, an acupuncture-tapping plate having attached needles, and an adjustable screw between said upper plate and said acupuncture-tapping plate; a buffer spring connecting said upper plate with said acupuncture-tapping plate, said buffer spring being attached on both sides of said adjustable screw; a buffer connector consisting of a main spring; a piston coupled to said upper plate; said main spring connecting the top of said adjustable screw with said piston; a driving member including an electrically operated rotatable member coupled to said piston for continuously moving said piston back and forth to drive said acupuncture-tapping member via said main spring; a minor spring mounted on both sides of said main spring for buffering said acupuncture-tapping member as it is driven by said piston; and means for supplying power to said driving member whereby said driving member drives said acupuncture-tapping plate by means of said buffer connector.

2. The apparatus as claimed in claim 1, wherein said needles of said acupuncture-tapping plate have a diameter of 0.5 to 5 mm and a length of 1 to 10 mm.

3. The apparatus as claimed in claim 1, wherein said needles of said tapping plate are selected from the group consisting of non-electromagnetic conductive needles, electromagnetic semiconductive needles, electric conductive needles, magnetic conductive needles, magnetic needles and magnets.

4. The apparatus as claimed in claim 1, having a support member coupled to said driving means for supporting said acupuncture-tapping apparatus at a preselected distance for the area being tapped.

* * * * *